US012351607B2

(12) United States Patent
Van Kampen et al.

(10) Patent No.: US 12,351,607 B2
(45) Date of Patent: Jul. 8, 2025

(54) HORN FLY VACCINE COMPOSITIONS AND METHODS OF MAKING SAME

(71) Applicant: TNG Pharmaceuticals, Inc., Louisville, KY (US)

(72) Inventors: Kent R. Van Kampen, Payson, UT (US); Serge Martinod, Groton, CT (US)

(73) Assignee: GNT Pharmaceuticals, Inc., Louisville, KY (US)

( * ) Notice: Subject to any disclaimer, the term of this patent is extended or adjusted under 35 U.S.C. 154(b) by 0 days.

(21) Appl. No.: 18/242,627

(22) Filed: Sep. 6, 2023

(65) Prior Publication Data

US 2024/0141000 A1    May 2, 2024

Related U.S. Application Data

(63) Continuation of application No. 16/771,800, filed as application No. PCT/US2018/065407 on Dec. 13, 2018, now Pat. No. 11,780,894.

(60) Provisional application No. 62/598,658, filed on Dec. 14, 2017.

(51) Int. Cl.
*C07K 14/435* (2006.01)
*A61K 39/00* (2006.01)

(52) U.S. Cl.
CPC .... *C07K 14/43577* (2013.01); *A61K 39/0003* (2013.01); *A61K 39/00* (2013.01); *A61K 2039/552* (2013.01); *A61K 2039/575* (2013.01); *C07K 2319/24* (2013.01); *C07K 2319/40* (2013.01)

(58) Field of Classification Search
None
See application file for complete search history.

(56) References Cited

U.S. PATENT DOCUMENTS

2012/0263742 A1* 10/2012 Cupp ................. A61K 39/0003
424/185.1
2024/0141000 A1*  5/2024 Van Kampen ..... A61K 39/0003

FOREIGN PATENT DOCUMENTS

WO    WO 2000/011172 A1    3/2000

OTHER PUBLICATIONS

Alignment of SEQ 1 with Geneseq db access No. BAE36442 by Cupp et al. 2012.*
Alignment of SEQ 2 with Geneseq db access No. BAE36443 by Cupp et al. 2012.*
Alignment of SEQ 3 with Geneseq db access No. BAE36444 by Cupp et al. 2012.*
Alignment of SEQ 4 with Geneseq db access No. BAE36441 by Cupp et al. 2012.*
Alignment of SEQ 5 with Geneseq db access No. BAE36440 by Cupp et al. 2012.*
Alignment of SEQ 10 with Geneseq db access No. BAE36442 by Cupp et al. 2012.*
Alignment of SEQ 12 with Geneseq db access No. BAE36443 by Cupp et al. 2012.*
Alignment of SEQ 6 with Geneseq db access No. BAE36443 by Cupp et al. 2012.*
Alignment of SEQ 7 with Geneseq db access No. BAE36442 by Cupp et al. 2012.*
Alignment of SEQ 8 with Geneseq db access No. BAE36441 by Cupp et al. 2012.*
Alignment of SEQ 9 with Geneseq db access No. BAE36443 by Cupp et al. 2012.*
Alignment of SEQ 11 with Geneseq db access No. BAE36442 by Cupp et al. 2012.*
Alignment of SEQ 13 with Geneseq db access No. BAE36444 by Cupp et al. 2012.*
Alignment of SEQ 14 with Geneseq db access No. BAE36451 by Cupp et al. 2012.*
Alignment of SEQ 15 with Geneseq db access No. BAE36451 by Cupp et al. 2012.*
Chiarella, Pieranna, et al., "Antigenic features of protein carries commonly used in immunization trials." Biotechnology letters 32.9 (2010): 1215-1221.
Cupp, Mary S., et al., "Evaluation of a recombinant salivary gland protein (thrombostasin) as a vaccine candidate to disrupt blood-feeding by horn flies." Vaccine 22.17-18 (2004): 2285-2297.
Cupp, MX, EW Cupp, C Navarre, D. Zhang, X Yue, L Todd, V Panangala. 2010. "Salivary gland thrombotstasin isoforms differentially regulate blood uptake of horn flies fed on control-and thrombostasin-vaccinated cattle." J. Med. Entomol. 47(4): 610-617.
Cupp, Mary. Vaccination of Cattle with Recombinant Salivary Proteins of Horn Flies (Haematobia Irritans Irritans). 000 0000: 20th International Conference of the World Association for the Advancement of Veterinary Parasitology (WAAVP 2005) (0000000). Christchurch (New Zealand). Oct. 16-20, 2005. World Association for the Advancement of Veterinary Parasitology (WAAVP). [Abstract only].

(Continued)

*Primary Examiner* — Shanon A. Foley
(74) *Attorney, Agent, or Firm* — Frost Brown Todd LLP; Nicole M. Tepe (57) ABSTRACT

Disclosed herein are fusion proteins comprising a truncated thrombostasin protein having at least 85% sequence homology to a thrombostasin protein, wherein the thrombostasin protein has a carboxy terminal deletion; and a fusion partner protein that is a non-thrombostasin protein. Further disclosed are vaccine compositions thrombostasin proteins having a comprising a carboxy terminal deletion, and methods for inhibiting a response to a thrombostasin protein in a host in need thereof, comprising the disclosed fusion proteins or vaccine compositions. Further disclosed are methods for the preparation of a fusion protein composition.

9 Claims, 3 Drawing Sheets
Specification includes a Sequence Listing.

(56) References Cited

OTHER PUBLICATIONS

Di Guana, Chu, et al. "Vectors that facilitate the expression and purification of foreign peptides in *Escherichia coli* by fusion to maltose-binding protein." Gene 67.1 (1988): 21-30.

International Search Report and Written Opinion dated Feb. 25, 2019 for International Application No. PCT/US2018/065407, 12 pages.

\* cited by examiner

Protocol 2a
Raw ELISA DATA Truncated Thrombostasin Recombinant Antigen

| Group | A | A | A | A | B | B | B | B | C | C | C |
|---|---|---|---|---|---|---|---|---|---|---|---|
| Day 0 | 758 | 763 | 767 | 768 | 760 | 762 | 765 | 766 | 759 | 761 | 764 |
| TB8N5 | 0 | 0.086 | 0 | 0.044 | 0 | 0 | 0.066 | 0 | 0 | 0.005 | 0.127 |
| TS9N5 | 0 | 0.171 | 0 | 0.019 | 0 | 0 | 0.031 | 0 | 0 | 0.058 | 0.102 |
| TS10N5 | 0 | 0.109 | 0 | 0.089 | 0 | 0 | 0.061 | 0 | 0 | 0.003 | 0.149 |
| TB5 | 0.129 | 0.053 | 0 | 0.12 | 0 | 0 | 0.106 | 0 | 2.492 | 0.084 | 0.189 |
| TS8 | 0.152 | 0.026 | 0 | 0.155 | 0 | 0 | 0.089 | 0 | 0 | 0.201 | 0.145 |
| TS9 | 1.255 | 0.037 | 0 | 0.244 | 0 | 0 | 0.085 | 0 | 0 | 0.058 | 0.137 |
| TS10 | 0.284 | 0.103 | 0 | 0.349 | 0 | 0 | 0.117 | 0 | 0.07 | 0.081 | 0.19 |
|  |  |  |  |  |  |  |  |  |  |  |  |
| Day 21 | 758 | 763 | 767 | 768 | 760 | 762 | 765 | 766 | 759 | 761 | 764 |
| TB8N5 | 1.481 | 1.45 | 0.998 | 1.164 | 0.756 | 0.266 | 0.632 | 0.809 | 0.042 | 0.016 | 0.022 |
| TS9N5 | 1.585 | 1.571 | 1.162 | 1.219 | 0.808 | 0.216 | 0.879 | 0.7 | 0.031 | 0.005 | 0.01 |
| TS10N5 | 1.703 | 1.686 | 1.164 | 1.129 | 0.904 | 0.293 | 0.926 | 0.812 | 0.048 | 0 | 0.042 |
| TB5 | 2.787 | 2.515 | 2.065 | 0.867 | 1.268 | 1.34 | 1.462 | 1.456 | 0.031 | 0.041 | 0.013 |
| TS8 | 2.213 | 2.723 | 2.221 | 1.353 | 1.358 | 1.625 | 1.727 | 1.552 | 0.044 | 0.072 | 0.024 |
| TS9 | 2.461 | 2.699 | 2.319 | 1.193 | 1.241 | 1.608 | 1.67 | 1.462 | 0.045 | 0.057 | 0.022 |
| TS10 | 2.477 | 2.515 | 2.21 | 1.16 | 1.25 | 1.635 | 1.477 | 1.428 | 0.064 | 0.11 | 0.036 |
|  |  |  |  |  |  |  |  |  |  |  |  |
| Day 35 | 758 | 763 | 767 | 768 | 760 | 762 | 765 | 766 | 759 | 761 | 764 |
| TB8N5 | 0.229 | 1.763 | 1.219 | 1.465 | 2.6 | 1.773 | 2.272 | 2.701 | 0.202 | 0.135 | 0.186 |
| TS9N5 | 0.224 | 1.986 | 1.369 | 1.544 | 2.833 | 1.963 | 2.47 | 2.602 | 0.195 | 0.161 | 0.193 |
| TS10N5 | 0.282 | 2.042 | 1.442 | 1.918 | 3.041 | 2.061 | 2.629 | 2.848 | 0.194 | 0.173 | 0.199 |
| TB5 | 0.356 | 3.215 | 2.783 | 2.609 | 3.509 | 3.469 | 3.509 | 3.509 | 0.23 | 0.151 | 0.213 |
| TS8 | 0.333 | 3.268 | 2.799 | 2.55 | 3.509 | 3.444 | 3.509 | 3.509 | 0.253 | 0.145 | 0.229 |
| TS9 | 0.354 | 3.444 | 2.876 | 2.541 | 3.509 | 3.509 | 3.509 | 3.509 | 0.225 | 0.152 | 0.222 |
| TS10 | 0.386 | 3.387 | 2.759 | 2.573 | 3.509 | 3.509 | 3.509 | 3.509 | 0.239 | 0.194 | 0.308 |

FIG. 3

HORN FLY VACCINE COMPOSITIONS AND METHODS OF MAKING SAME

CROSS-REFERENCE TO RELATED APPLICATIONS

This application is a continuation of U.S. application Ser. No. 16/771,800, entitled "Horn Fly Vaccine Compositions and Methods of Making Same," filed Jun. 11, 2020, which is a National Stage Entry of International Application No. PCT/US18/65407, entitled "Vaccine Compositions and Methods of Making Same," filed Dec. 13, 2018 which claims priority to and benefit of U.S. Provisional Application No. 62/598,658, entitled "Thrombostasins for Horn Fly Vaccine Production," filed Dec. 14, 2017, the contents of which are incorporated in their entirety for all purposes.

REFERENCE TO SEQUENCE LISTING

A Sequence Listing submitted as an ST26 XML file via EFS-Web is hereby incorporated by reference in accordance with 35 U.S.C. § 1.52(e). The name of the XML file for the Sequence Listing is TNG U.S. Pat. No. 1,824,627 SL.xml the date of the creation of the XML file is Oct. 21, 2023, and the size of the XML file is 32,768 bytes.

BACKGROUND

The horn fly is a major problem affecting cattle in the US and other parts of the world like Latin America. It is estimated that the economic impact on US livestock production is greater than $1 billion per year.

The horn fly produces in its saliva a toxin called Thrombostasin. This toxin, once injected after the bite, interferes with the blood coagulation of cattle causing anemia and allowing the fly to suck blood easily. A Thrombostasin vaccine is one method by which the biological activity of Thrombostasin can be neutralized. When injected into the animal, the vaccine is effective only after an immune response to TS is elicited, and when antibodies produced in response to vaccination protect against disruption of normal clotting function at bite sites.

Vaccine trials performed in cattle in 2004 and 2005 consisted of the TS proteins produced in *E. coli* through recombinant DNA technology. Vaccines were prepared using recombinant TS isoforms TB8 and TS9 (Cupp et al, 2004, Cupp et al, 2005)) and inoculated by intramuscular route of vaccination to elicit an antibody response. Cattle, injected with the vaccine containing the TS isoforms, developed antibodies specific to TS, and decreased blood uptake by horn flies was observed in comparison to cattle vaccinated with ovalbumin. In a follow-up trial reported in 2010, cattle vaccinated with recombinant isoforms TB8 and TS9 again developed antibodies specific to TS, and demonstrated a significant decrease in blood uptake by horn flies during a 20-minute feeding time frame.

While these studies suggest success of a Thrombostasin vaccine, methods of effectively making the vaccine in amounts sufficient to provide the vaccine on a larger scale basis have not been available. Specifically, prior to Applicant's invention, it has not been possible to harvest enough antigen from the fly to produce a commercial vaccine, thus limiting the ability to produce an effective vaccine for the control of the horn fly and its effect on cattle populations. The instant invention seeks to address one or more of the aforementioned needs in the art.

BRIEF SUMMARY

Disclosed herein are fusion proteins comprising a truncated thrombostasin protein having at least 85% sequence homology to a thrombostasin protein, wherein the thrombostasin protein has a carboxy terminal deletion; and a fusion partner protein that is a non-thrombostasin protein. Further disclosed are vaccine compositions thrombostasin proteins having a comprising a carboxy terminal deletion, and methods for inhibiting a response to a thrombostasin protein in a host in need thereof, comprising the disclosed fusion proteins or vaccine compositions. Further disclosed are methods for the preparation of a fusion protein composition.

BRIEF DESCRIPTION OF THE DRAWINGS

Those of skill in the art will understand that the drawings, described below, are for illustrative purposes only. The drawings are not intended to limit the scope of the present teachings in any way.

FIG. 3 depicts the delay in recalcification time induced by horn fly saliva test

DETAILED DESCRIPTION

Definitions

Unless otherwise noted, terms are to be understood according to conventional usage by those of ordinary skill in the relevant art. In case of conflict, the present document, including definitions, will control. Preferred methods and materials are described below, although methods and materials similar or equivalent to those described herein may be used in practice or testing of the present invention. All publications, patent applications, patents and other references mentioned herein are incorporated by reference in their entirety. The materials, methods, and examples disclosed herein are illustrative only and not intended to be limiting.

As used herein and in the appended claims, the singular forms "a," "and," and "the" include plural referents unless the context clearly dictates otherwise. Thus, for example, reference to "a method" includes a plurality of such methods and reference to "a dose" includes reference to one or more doses and equivalents thereof known to those skilled in the art, and so forth.

The term "about" or "approximately" means within an acceptable error range for the particular value as determined by one of ordinary skill in the art, which will depend in part on how the value is measured or determined, e.g., the limitations of the measurement system. For example, "about" may mean within 1 or more than 1 standard deviation, per the practice in the art. Alternatively, "about" may mean a range of up to 20%, or up to 10%, or up to 5%, or up to 1% of a given value. Alternatively, particularly with respect to biological systems or processes, the term may mean within an order of magnitude, preferably within 5-fold, and more preferably within 2-fold, of a value. Where particular values are described in the application and claims, unless otherwise stated the term "about" meaning within an acceptable error range for the particular value should be assumed.

As used herein, the term "effective amount" means the amount of one or more active components that is sufficient to show a desired effect. This includes both therapeutic and prophylactic effects. When applied to an individual active ingredient, administered alone, the term refers to that ingredient alone. When applied to a combination, the term refers to combined amounts of the active ingredients that result in the therapeutic effect, whether administered in combination, serially or simultaneously.

"Sequence identity" as used herein indicates a nucleic acid sequence that has the same nucleic acid sequence as a reference sequence, or has a specified percentage of nucleotides that are the same at the corresponding location within a reference sequence when the two sequences are optimally aligned. For example, a nucleic acid or amino acid sequence may have at least 50%, 60%, 70%, 75%, 80%, 85%, 90%, 95%, 96%, 97%, 98%, 99%, or 100% identity to the reference nucleic acid or amino acid sequence. The length of comparison sequences will generally be at least 5 contiguous nucleotides, or at least 10, 11, 12, 13, 14, 15, 16, 17, 18, 19, 20, 21, 22, 23, 24, or 25 contiguous nucleotides, or the full-length nucleotide or amino acid sequence. Sequence identity may be measured using sequence analysis software on the default setting (e.g., Sequence Analysis Software Package of the Genetics Computer Group, University of Wisconsin Biotechnology Center, 1710 University Avenue, Madison, Wis. 53705). Such software may match similar sequences by assigning degrees of homology to various substitutions, deletions, and other modifications.

Prior to Applicant's invention, it has not been possible to harvest enough antigens from the horn fly to produce a commercial vaccine. One possible solution is to clone and express the protein in, for example $E.$ $coli$ using a plasmid vector. Despite many attempts, however, Applicant has discovered that it has not been not possible to produce enough antigens using the full-length Thrombostasin genes.

Disclosed herein are fusion proteins that may comprise a truncated thrombostasin protein having at least 85% sequence homology to a thrombostasin protein, wherein the thrombostasin protein comprises a carboxy terminal deletion; and a fusion partner protein that may comprise a non-thrombostasin protein component. By "fusion partner protein" it is meant an amino acid sequence that is fused to the thrombostasin protein and which may be used to improve yield of the fusion protein during the manufacturing process. Generally, and as contemplated herein, the fusion partner protein is contiguous with the thrombostasin protein, in that the fusion partner protein and thrombostasin protein are part of a single sequence. The sequences may, in certain aspects, use additional linker sequence which connect the fusion partner protein and thrombostasin protein.

In one aspect, the fusion partner protein is a non-thrombostasin protein, in that it is does not comprise a sequence having substantial sequence identity to a thrombostasin protein. In one aspect, the truncated thrombostasin protein may be as immunogenic in mammals as a native, non-truncated thrombostasin protein. In other aspects, the immunogenicity may be substantially the same as native, non-truncated thrombostasin protein. In one aspect, the truncated thrombostasin protein produces biologically active antibodies that interfere with the anti-clotting activity of natural thrombostasin from horn fly.

In one aspect, the thrombostasin protein may be selected from TS9 (SEQ ID NO: 1), TS10 (SEQ ID NO: 2), TB8 (SEQ ID NO: 3), TS8 (SEQ ID NO: 4), TS2 (SEQ ID NO: 5), GTS 1 (SEQ ID NO: 6), GTS 2 (SEQ ID NO: 7), GTS 3 (SEQ ID NO: 8), GTS 4 (SEQ ID NO: 9), GTS 5 (SEQ ID NO: 10), GTS 6 (SEQ ID NO: 11), and GTS 7 (SEQ ID NO: 12). In one aspect, the remaining portion of the truncated thrombostasin protein (i.e., the sequence that remains after an N terminal deletion) may be at least 80%, 81%, 82%, 83%, 84%, 85%, 86%, 87%, 88%, 89%, 90%, 91%, 92%, 93%, 94%, 95%, 96%, 97%, 98%, or 99% identical to a sequence selected from any of SEQ ID NOs: 1-12, wherein the thrombostasin protein is capable of being bound by an antibody that specifically binds to a thrombostasin protein selected from SEQ ID NOs: 1-12.

In one aspect, the carboxy terminal deletion may be a deletion of at least 5 amino acids, or at least 6 amino acids, or at least 6 amino acids, or at least 7 amino acids, or at least 8 amino acids, or at least 9 amino acids, or at least 10 amino acids, or at least 11 amino acids, or at least 12 amino acids, or at least 13 amino acids, or at least 14 amino acids, or at least 15 amino acids, or at least 16 amino acids, or at least 17 amino acids, or at least 18 amino acids, or at least 19 amino acids, or at least 20 amino acids, or from about 10 to 35 amino acids, or from about 15 to 30 amino acids, or about 20 to about 25 amino acids, or about 30 amino acids. In one aspect, the truncated thrombostasin protein may be selected from SEQ ID NO: 13, SEQ ID NO: 14, SEQ ID NO: 15, and a combination thereof.

In one aspect, the fusion partner protein may be selected from maltose binding protein (MBP), protein for antigen fusion (PAF), C reactive protein (CRP) or a fragment thereof, (3-galactosidase, glutathione-S-transferase, poly-histidine, myelin basic protein (MBP1-9) or a fragment thereof, chicken egg white ovalbumin (OVA) and combinations thereof. Suitable fusion partner proteins for the proteins of the invention are well known to those of skill in the art and include, among others, 0-galactosidase, glutathione-S-transferase, poly-histidine and maltose binding protein.

In one aspect, a vaccine composition is disclosed. The vaccine composition may comprise a thrombostasin sequence having a deletion at the C terminal end, wherein said deletion is the last 35 amino acids, the last 34 amino acids, the last 33 amino acids, the last 32 amino acids, the last 31 amino acids, the last 30 amino acids, the last 29 amino acids, the last 28 amino acids, the last 27 amino acids, the last 26 amino acids, the last 25 amino acids, the last 24 amino acids, the last 23 amino acids, the last 22 amino acids, the last 21 amino acids, or the last 20 amino acids. the vaccine composition may further comprising a fusion partner protein.

In one aspect, the vaccine composition may comprise a plurality of fusion proteins comprising a thrombostasin protein, for example, a plurality of fusion proteins including a truncated TS9 protein, a truncated TS10 protein, or one or both of a truncated TB8 protein or truncated TS8 protein. In one aspect, the vaccine composition may comprise a truncated thrombostasin protein and fusion partner protein sequence of SEQ ID NO 16, SEQ ID NO 18, SEQ ID NO 20, SEQ ID NO 21, SEQ ID NO 22, SEQ ID NO 23, or a combination thereof.

In one aspect, the fusion protein of the vaccine composition may be present in an amount sufficient to elicit a biological response in a host. The vaccine composition may further comprising a pharmaceutically acceptable carrier and/or an adjuvant. As used herein, the term "adjuvant" typically refers to a class of substance that can increase the magnitude of the immune response elicited by the fusion protein conjugate beyond that which would be expected, either from the protein alone or from the fusion carrier protein conjugate as described herein in the absence of an adjuvant. In an embodiment, the pharmaceutically acceptable carrier includes an adjuvant. There is no specific limitation on kinds of the adjuvants, examples of which can include but be not limited to aluminum gel adjuvant, oil adjuvant (for example, Freund's complete adjuvant, Freund's incomplete adjuvant and so on) or any combination thereof. Suitable adjuvants will be known to persons skilled in the art. Non-limiting examples of suitable adjuvants include aluminum salts (e.g. aluminum hydroxide, aluminum phosphate and potassium aluminum sulfate (also referred to as Alum)), liposomes, virosomes, water-in-oil or oil-in-water emulsions (e.g. Freund's adjuvant, Montanide®, MF59® and AS03), 3-O-desacyl-4'-monophosphoryl lipid A (MPL) and adjuvants containing MPL (e.g. AS01, AS02 and AS04) and saponin-based adjuvants. Saponin-based adjuvants include saponins or saponin derivatives from, for example, Quillaja saponaria, Panax ginseng Panax notoginseng, Panax quinquefolium, Platycodon grandiflorum, Polygala senega, Polygala tenuifolia, Quillaja brasiliensis, Astragalus membranaceus and Achyranthes bidentata. Exemplary saponin-based adjuvants include iscoms, iscom matrix, ISCOMATRIX™ adjuvant, Matrix M™ adjuvant, Matrix C™ adjuvant, Matrix Q™ adjuvant, AbISCO®-100 adjuvant, AbISCO®-300 adjuvant, ISCOPREP™, an ISCOPREP™ derivative, adjuvant containing ISCOPREP™ or an ISCOPREP™ derivative, QS-21, a QS-21 derivative, and an adjuvant containing QS-21 or a QS21 derivative. The vaccine composition as herein described can also be associated with immumodulatory agents, including, for example, cytokines, chemokines and growth factors. Mixtures of two or more adjuvants within the same vaccine composition are also contemplated herein. Suitable pharmaceutically acceptable carriers (e.g. excipients, diluents, etc.). will be known to persons skilled in the art. For example, a variety of aqueous (pharmaceutically acceptable) carriers may be used, such as buffered water, 0.4% saline, 0.3% glycine, hyaluronic acid and the like. These compositions may be sterilized by conventional, well known sterilization techniques or may be sterile-filtered. The resulting aqueous solutions may be packaged for use as is or lyophilized, the lyophilized preparation being combined with a sterile solution prior to administration. The compositions may further comprise pharmaceutically acceptable auxiliary substances as required to approximate physiological conditions, such as pH-adjusting and buffering agents, tonicity-adjusting agents, wetting agents and the like, for example sodium acetate, sodium lactate, sodium chloride, potassium chloride, calcium chloride, sorbitan monolaurate, triethanolamine oleate, sucrose or other carbohydrates, among many others. Suitable methods for preparing parenterally administrable compounds will be known or apparent to those skilled in the art. The pharmaceutical composition may be in a form suitable for parenteral administration (e.g., subcutaneous, intramuscular or intravenous injection) or in an aerosol form suitable for administration by inhalation, such as by intranasal inhalation or oral inhalation. The pharmaceutical compositions described herein may also be provided in a kit. The kit may comprise additional components to assist in performing the methods as herein described, such as administration device(s), excipients(s), and/or diluent(s). The kits may include containers for housing the various components and instructions for using the kit components in such methods.

The vaccine or pharmaceutical compositions, as described herein, are typically administered in an "effective amount"; that is, an amount effective to elicit any one or more inter alia of a therapeutic or prophylactic effect. Persons skilled in the art would be able, by routine experimentation, to determine an effective, non-toxic amount to include in a pharmaceutical composition or to be administered for the desired outcome. In general, the vaccine and/or pharmaceutical compositions, as disclosed herein, can be administered in a manner compatible with the route of administration and physical characteristics of the recipient and in such a way that it elicits the desired effect(s) (i.e. therapeutically effective, immunogenic and/or protective). For example, the appropriate dosage of a composition may depend on a variety of factors including, but not limited to, a subject's physical characteristics (e.g., age, weight, sex). In some instances, it may be desirable to have several or multiple administrations of the vaccine and/or pharmaceutical compositions, as herein described. For example, the compositions may be administered 1, 2, 3, 4, 5, 6, 7, 8, 9, 10, or more times. The administrations may be from about one day intervals to about twelve-week intervals, and in certain embodiments from about one to about four-week intervals. Periodic re-administration may be required to achieve a desirable therapeutic result, such as a reduction in tumour size and/or a reduction in the occurrence of metastases. It will also be apparent to persons skilled in the art that the optimal course of administration can be ascertained using conventional course of treatment or efficacy or immune status determination tests.

In one aspect, the fusion protein or vaccine composition as disclosed herein may be injected intramuscularly, subcutaneously or any other route of administration.

In one aspect, a method for inhibiting a response to a thrombostasin protein in a host in need thereof is disclosed. In this aspect, the method may comprise the step of administering a therapeutically effective amount of a fusion protein or vaccine composition as described herein to the host. The host may be a mammal, in particular, cattle.

In one aspect, a method for preparation of a thrombostasin deletion mutant fusion protein composition is disclosed. The method may comprise the steps of generating a plasmid for expressing one or more fusion proteins as disclosed herein; causing the plasmid to express the one or more fusion proteins within a host cell; and collecting the one or more fusion proteins from said host cell. In one aspect, the fusion protein may be produced in in *E. coli*. In other aspects, the fusion protein may be produced in any cell production system, such as, for example, bacteria, fungi, insects or mammalian cells. In one aspect, the fusion protein may be produced by chemical peptide synthesis.

Pharmaceutical Compositions

In one aspect, active agents provided herein may be administered in an dosage form selected from intravenous or subcutaneous or intramuscular unit dosage form, oral, parenteral, intravenous, intramuscular, and subcutaneous. In some embodiments, active agents provided herein may be formulated into liquid preparations for, e.g., oral administration. Suitable forms include suspensions, syrups, elixirs, and the like. In some embodiments, unit dosage forms for oral administration include tablets and capsules. Unit dosage forms configured for administration once a day; however, in certain embodiments it may be desirable to configure the unit dosage form for administration twice a day, or more.

In one aspect, pharmaceutical compositions are isotonic with the blood or other body fluid of the recipient. The isotonicity of the compositions may be attained using sodium tartrate, propylene glycol or other inorganic or organic solutes. An example includes sodium chloride. Buffering agents may be employed, such as acetic acid and salts, citric acid and salts, boric acid and salts, and phosphoric acid and salts. Parenteral vehicles include sodium chloride solution, Ringer's dextrose, dextrose and sodium chloride, lactated Ringer's or fixed oils. Intravenous vehicles include fluid and nutrient replenishers, electrolyte replenishers (such as those based on Ringer's dextrose), and the like.

Viscosity of the pharmaceutical compositions may be maintained at the selected level using a pharmaceutically acceptable thickening agent. Methylcellulose is useful because it is readily and economically available and is easy to work with. Other suitable thickening agents include, for example, xanthan gum, carboxymethyl cellulose, hydroxypropyl cellulose, carbomer, and the like. In some embodiments, the concentration of the thickener will depend upon the thickening agent selected. An amount may be used that will achieve the selected viscosity. Viscous compositions are normally prepared from solutions by the addition of such thickening agents.

A pharmaceutically acceptable preservative may be employed to increase the shelf life of the pharmaceutical compositions. Benzyl alcohol may be suitable, although a variety of preservatives including, for example, parabens, thimerosal, chlorobutanol, or benzalkonium chloride may also be employed. A suitable concentration of the preservative is typically from about 0.02% to about 2% based on the total weight of the composition, although larger or smaller amounts may be desirable depending upon the agent selected. Reducing agents, as described above, may be advantageously used to maintain good shelf life of the formulation.

In one aspect, active agents provided herein may be in admixture with a suitable carrier, diluent, or excipient such as sterile water, physiological saline, glucose, or the like, and may contain auxiliary substances such as wetting or emulsifying agents, pH buffering agents, gelling or viscosity enhancing additives, preservatives, flavoring agents, colors, and the like, depending upon the route of administration and the preparation desired. See, e.g., "Remington: The Science and Practice of Pharmacy", Lippincott Williams & Wilkins; 20th edition (Jun. 1, 2003) and "Remington's Pharmaceutical Sciences," Mack Pub. Co.; 18th and 19th editions (December 1985, and June 1990, respectively). Such preparations may include complexing agents, metal ions, polymeric compounds such as polyacetic acid, polyglycolic acid, hydrogels, dextran, and the like, liposomes, microemulsions, micelles, unilamellar or multilamellar vesicles, erythrocyte ghosts or spheroblasts. Suitable lipids for liposomal formulation include, without limitation, monoglycerides, diglycerides, sulfatides, lysolecithin, phospholipids, saponin, bile acids, and the like. The presence of such additional components may influence the physical state, solubility, stability, rate of in vivo release, and rate of in vivo clearance, and are thus chosen according to the intended application, such that the characteristics of the carrier are tailored to the selected route of administration.

For oral administration, the pharmaceutical compositions may be provided as a tablet, aqueous or oil suspension, dispersible powder or granule, emulsion, hard or soft capsule, syrup or elixir. Compositions intended for oral use may be prepared according to any method known in the art for the manufacture of pharmaceutical compositions and may include one or more of the following agents: sweeteners, flavoring agents, coloring agents and preservatives. Aqueous suspensions may contain the active ingredient in admixture with excipients suitable for the manufacture of aqueous suspensions. Lubrimayts, such as stearic acid or magnesium or calcium salts thereof, polytetrafluoroethylene, liquid paraffin, vegetable oils and waxes, sodium lauryl sulfate, magnesium lauryl sulfate, polyethylene glycol, starch, talc, pyrogenic silica, hydrated silicoaluminate, and the like, may be included in tablet formulations. Surfactants may also be employed, for example, anionic detergents such as sodium lauryl sulfate, dioctyl sodium sulfosuccinate and dioctyl sodium sulfonate, cationic such as benzalkonium chloride or benzethonium chloride, or nonionic detergents such as polyoxyethylene hydrogenated castor oil, glycerol monostearate, polysorbates, sucrose fatty acid ester, methyl cellulose, or carboxymethyl cellulose. Controlled release formulations may be employed wherein the active agent or analog(s) thereof is incorporated into an inert matrix that permits release by either diffusion or leaching mechanisms. Slowly degenerating matrices may also be incorporated into the formulation. Other delivery systems may include timed release, delayed release, or sustained release delivery systems. Coatings may be used, for example, nonenteric materials such as methyl cellulose, ethyl cellulose, hydroxyethyl cellulose, methylhydroxy-ethyl cellulose, hydroxypropyl cellulose, hydroxypropyl-methyl cellulose, sodium carboxymethyl cellulose, providone and the polyethylene glycols, or enteric materials such as phthalic acid esters. Dyestuffs or pigments may be added for identification or to characterize different combinations of active agent doses. When administered orally in liquid form, a liquid carrier such as water, petroleum, oils of animal or plant origin such as peanut oil, mineral oil, soybean oil, or sesame oil, or synthetic oils may be added to the active ingredient(s). Physiological saline solution, dextrose, or other saccharide solution, or glycols such as ethylene glycol, propylene glycol, or polyethylene glycol are also suitable liquid carriers. The pharmaceutical compositions may also be in the form of oil-in-water emulsions. The oily phase may be a vegetable oil, such as olive or arachis oil, a mineral oil such as liquid paraffin, or a mixture thereof. Suitable emulsifying agents include naturally-occurring gums such as gum acacia and gum tragamayth, naturally occurring phosphatides, such as soybean lecithin, esters or partial esters derived from fatty acids and hexitol anhydrides, such as sorbitan mono-oleate, and condensation products of these partial esters with ethylene oxide, such as polyoxyethylene sorbitan mono-oleate. The emulsions may also contain sweetening and flavoring agents.

Pulmonary delivery of the active agent may also be employed. The active agent may be delivered to the lungs while inhaling and traverses across the lung epithelial lining to the blood stream. A wide range of mechanical devices designed for pulmonary delivery of therapeutic products may be employed, including but not limited to nebulizers, metered dose inhalers, and powder inhalers, all of which are familiar to those skilled in the art. These devices employ formulations suitable for the dispensing of active agent. Typically, each formulation is specific to the type of device employed and may involve the use of an appropriate propellant material, in addition to diluents, adjuvants, and/or carriers useful in therapy. In some embodiments, an active agent provided herein may be administered by intravenous, parenteral, or other injection, in the form of a pyrogen-free, parenterally acceptable aqueous solution or oleaginous suspension. Suspensions may be formulated according to methods well known in the art using suitable dispersing or wetting agents and suspending agents. The preparation of acceptable aqueous solutions with suitable pH, isotonicity, stability, and the like, is within the skill in the art. In some embodiments, a pharmaceutical composition for injection may include an isotonic vehicle such as 1,3-butanediol, water, isotonic sodium chloride solution, Ringer's solution, dextrose solution, dextrose and sodium chloride solution, lactated Ringer's solution, or other vehicles as are known in the art. In addition, sterile fixed oils may be employed conventionally as a solvent or suspending medium. For this purpose, any bland fixed oil may be employed including synthetic mono or diglycerides. In addition, fatty acids such as oleic acid may likewise be used in the formation of injectable preparations. The pharmaceutical compositions may also contain stabilizers, preservatives, buffers, antioxidants, or other additives known to those of skill in the art.

The duration of the injection may be adjusted depending upon various factors, and may comprise a single injection administered over the course of a few seconds or less, to 0.5, 0.1, 0.25, 0.5, 0.75, 1, 2, 3, 4, 5, 6, 7, 8, 9, 10, 11, 12, 13, 14, 15, 16, 17, 18, 19, 20, 21, 22, 23, or 24 hours or more of continuous intravenous administration.

In some embodiments, active agents provided herein may additionally employ adjunct components conventionally found in pharmaceutical compositions in their art-established fashion and at their art-established levels. Thus, for example, the compositions may contain additional compatible pharmaceutically active materials for combination therapy, such as insecticides or insect growth regulators and the like, anti-anemic drugs such as iron dextran, ferrous sulfate, EPO, deferoxamine, folic acid, and vitamin B12, or may contain materials useful in physically formulating various dosage forms, such as excipients, dyes, thickening agents, stabilizers, preservatives or antioxidants.

In some embodiments, the active agents provided herein may be provided to an administering physician or other health care professional in the form of a kit. The kit is a package which houses a container which contains the active agent(s) in a suitable pharmaceutical composition, and instructions for administering the pharmaceutical composition to a subject. The kit may optionally also contain one or more additional therapeutic agents currently employed for treating one or more disease states as described herein. For example, a kit containing one or more compositions comprising active agents provided herein in combination with one or more additional active agents may be provided, or separate pharmaceutical compositions containing an active agent as provided herein and additional therapeutic agents may be provided. The kit may also contain separate doses of a active agent provided herein for serial or sequential administration. The kit may optionally contain one or more diagnostic tools and instructions for use. The kit may contain suitable delivery devices, e.g., syringes, and the like, along with instructions for administering the active agent(s) and any other therapeutic agent. The kit may optionally contain instructions for storage, reconstitution (if applicable), and administration of any or all therapeutic agents included. The kits may include a plurality of containers reflecting the number of administrations to be given to a subject.

Examples

The following non-limiting examples are provided to further illustrate embodiments of the invention disclosed herein. It should be appreciated by those of skill in the art that the techniques disclosed in the examples that follow represent approaches that have been found to function well in the practice of the invention, and thus may be considered to constitute examples of modes for its practice. However, those of skill in the art should, in light of the present disclosure, appreciate that many changes may be made in the specific embodiments that are disclosed and still obtain a like or similar result without departing from the spirit and scope of the invention.

Example 1. The Following Yield were Obtained with the Following Systems in Flasks or Fermenters

| CLONE | YIELD |
| --- | --- |
| BL-21 *Escherichia coli*, pVEXK-H6-TS9 | 0 |
| *Escherichia coli*, Rosetta TS9 | 10 µg/ml |
| BL-21 *Escherichia coli*, pVEXKB-Ntag-TB8 | 0 |
| BL-21 *Escherichia coli*, pVEXK-TS9-CtagH8 | 0 |

In typical recombinant protein production, the recombinant protein will represent 15-30% of the total protein present. Fermentations of the Rosetta TS9 strain a yielded TS9 concentrations anywhere from 0.1 to 0.4% of the total protein. Scaling up this construct or another similar TS9 or TB8 construct, would require a significant increase in the production fermentation titer in order to make it an economically viable process. Accordingly, new discoveries have been needed in order to overcome this major technical hurdle for producing recombinant Thrombostasin protein.

Data collected by Applicant has further elucidated the toxic effects of Thrombostasin on biological systems. During procedures to clone and express the isoforms of Thrombostasin in highly regulated expression systems for large scale production of recombinant proteins, depending on the expression system, it has been found that all four isoforms of Thrombostasin (TB8, TS8, TS9, or TS10) when cloned into various host/plasmid expression systems cause cell death, lysis, or aberrant growth.

In order to overcome this problem, fusion protein genes were added to the TS genes into an *E. coli* expression vector. Two fusion proteins provided similar results summarized in the Table below for two isoforms of Thrombostasin TS9 and TB8. As the yields were still not high enough for commercial use, a small deletion was made at the C terminal portion of the Thrombostasin gene. In one aspect, the deletion may be about 30 amino acids (in one aspect, the deletion may be LRARFNKFMA KFTSLFGRRR GVDVPNAAHH (SEQ ID NO 24) for TS9). Surprisingly, this deletion boosted the production of the protein in tissue culture flasks and fermenter. Exemplary fusion proteins include MBP and PAF. MBP stands for maltose binding protein and is well known in the art, see, for example, di Guan, C; Li, P; Riggs, PD; Inouye, H (1988). "Vectors that facilitate the expression and purification of foreign peptides in *Escherichia coli* by fusion to maltose-binding protein". Gene. 67 (1): 21-30. PAF (Proteins for Antigen Fusion) is an example of another fusion protein that may be used with the instant disclosure.

| TS Antigen | Method of Production | Yield in Flask | Yield in Fermenter |
| --- | --- | --- | --- |
| TS9 | TS9 | Very poor | |
| | PAF TS9 | 10 mg/ml | 70 mg/ml |
| | PAF TS9N5 | 40 mg/ml | 100 mg/ml |
| | MBPTS9 | 10 mg/ml | |
| TB8 | TB8 | No expression | |
| | PAFTB8 | 10 mg/ml | |
| | PAFTB8N5 | 25 mg/ml | |

Exemplary amino acid sequences of the newly created proteins are as follows. It should be understood by one of ordinary skill in the art that a suitable composition may include some variation while still maintaining function, for example, including sequences having sequence identity to the disclosed sequences of about 85%, 86%, 87%, 88%, 89%, 90%, 91%, 92%, 93%, 94%, 95%, 96%, 97%, 98%, 99%, or any range of the foregoing.

MBPTS9: Protein length=556 MW=61501.0. The MBP sequence is indicated in bold. The PAF sequence is indicated in bold/italics. Regular text represents the thrombostasin protein.

```
                                          (SEQ ID NO 16)
MKIEEGKLVI WINGDKGYNG LAEVGKKFEK DTGIKVTVEH

PDKLEEKFPQ VAATGDGPDI IFWAHDRFGG YAQSGLLAEI

TPDKAFQDKL YPFTWDAVRY NGKLIAYPIA VEALSLIYNK

DLLPNPPKTW EEIPALDKEL KAKGKSALMF NLQEPYFTWP

LIAADGGYAF KYENGKYDIK DVGVDNAGAK AGLTFLVDLI

KNKHMNADTD YSIAEAAFNK GETAMTINGP WAWSNIDTSK

VNYGVTVLPT FKGQPSKPFV GVLSAGINAA SPNKELAKEF

LENYLLTDEG LEAVNKDKPL GAVALKSYEE ELAKDPRIAA

TMENAQKGEI MPNIPQMSAF WYAVRTAVIN AASGRQTVDE

ALKDAQTNSS SNNNNNNNNN NLGIEGRISE FGS QNVLSGR

RQHGAQGLSG YSGDNDWGYY GEAGAPGSDY SGSSGQWAPL

DFDYNSLPGL SGYNHEQQDY EEDSYRHVRS AGPITLQLDD

DDDDDSGIPI FEMDDEDEDS NDNQKFPLSF ERFPENEKNQ

EGLRARFNKF MAKFTSLFGR RGVDVPNAA HHHHHH.

PAFTS9 Protein length = 304 Molecular weight
34101.2.
                                          (SEQ ID NO 17)
MKLTIESTPF NVAEGKEVLL LVHNLPQHLF GYSWYKGERV

DGNRQIIGYV IGTQQATPGP AYSGREIIYP NASLLIQNII

QNDTGFYTLH VIKSDLVNEE ATGQFRVYPE LPKPSISSNN

SKPVEDKDAV AFTCEPETQD A QNLVSGRRQ HGAQGLSGYS

GDNDWGYYGE AGAPGSDYSG SSGQWAPLDF DYNSLPGLSG

YNHEQQDYEE DSYRHVRSAG PITLQLDDDD DDDSGIPIFE

MDDEDEDSND NQKFPLSFER FPENEKNQEG LRARFNKFMA

KFTSLFGRRR GVDVPNAAHH HHHH

PAFTS9N5 Protein length = 276 MW = 30892.0.
                                          (SEQ ID NO 18)
MKLTIESTPF NVAEGKEVLL LVHNLPQHLF GYSWYKGERV

DGNRQIIGYV IGTQQATPGP AYSGREIIYP NASLLIQNII

QNDTGFYTLH VIKSDLVNEE ATGQFRVYPE LPKPSISSNN

SKPVEDKDAV AFTCEPETQD A QNLVSGRRQ HGAQGLSGYS

GDNDWGYYGE AGAPGSDYSG SSGQWAPLDF DYNSLPGLSG

YNHEQQDYEE DSYRHVRSAG PITLQLDDDD DDDSGIPIFE

MDDEDEDSND NQKFPLSFER FPENEKNQEG HHHHHH.

PAFTB8 Protein length = 304 MW=34040.2.
                                          (SEQ ID NO 19)
MKLTIESTPF NVAEGKEVLL LVHNLPQHLF GYSWYKGERV

DGNRQIIGYV IGTQQATPGP AYSGREIIYP NASLLIQNII

QNDTGFYTLH VIKSDLVNEE ATGQFRVYPE LPKPSISSNN

SKPVEDKDAV AFTCEPETQD A QNLVSGRRQ HGAQGLSGYS

GDNDWGYYGE AGAPGSDYSG SSGQWAPLDF DYNSLPGLSG

YNHEQQDYEE DSYRHVRSAG PITLQLDDDD DDDSGIPIFE

MDDEDVDSND NQKFPLSFER FPENEKNQVG LRARFNKFMA

KFTSLFGRRR GVNVPNAAHH HHHH

PAFTB8N5 Protein length = 276 MW = 30833.0.
                                          (SEQ ID NO 20)
MKLTIESTPF NVAEGKEVLL LVHNLPQHLF GYSWYKGERV

DGNRQIIGYV IGTQQATPGP AYSGREIIYP NASLLIQNII

QNDTGFYTLH VIKSDLVNEE ATGQFRVYPE LPKPSISSNN

SKPVEDKDAV AFTCEPETQD A QNLVSGRRQ HGAQGLSGYS

GDNDWGYYGE AGAPGSDYSG SSGQWAPLDF DYNSLPGLSG

YNHEQQDYEE DSYRHVRSAG PITLQLDDDD DDDSGIPIFE

MDDEDVDSND NQKFPLSFER FPENEKNQVG HHHHHH.
```

A similar process can be applied to all isoforms of Thrombostasin, for example:

```
MBPTS9N5 Protein length = 528 MW = 58292.8.
                                          (SEQ ID NO 21)
MKIEEGKLVI WINGDKGYNG LAEVGKKFEK DTGIKVTVEH

PDKLEEKFPQ VAATGDGPDI IFWAHDRFGG YAQSGLLAEI

TPDKAFQDKL YPFTWDAVRY NGKLIAYPIA VEALSLIYNK

DLLPNPPKTW EEIPALDKEL KAKGKSALMF NLQEPYFTWP

LIAADGGYAF KYENGKYDIK DVGVDNAGAK AGLTFLVDLI

KNKHMNADTD YSIAEAAFNK GETAMTINGP WAWSNIDTSK

VNYGVTVLPT FKGQPSKPFV GVLSAGINAA SPNKELAKEF

LENYLLTDEG LEAVNKDKPL GAVALKSYEE ELAKDPRIAA

TMENAQKGEI MPNIPQMSAF WYAVRTAVIN AASGRQTVDE

ALKDAQTNSS SNNNNNNNNN NLGIEGRISE FGS QNVLSGR

RQHGAQGLSG YSGDNDWGYY GEAGAPGSDY SGSSGQWAPL

DFDYNSLPGL SGYNHEQQDY EEDSYRHVRS AGPITLQLDD

DDDDDSGIPI FEMDDEDEDS NDNQKFPLSF ERFPENEKNQ

EGHHHHHH.

MBPTS10N5 Protein length = 528 MW = 58262.8.
                                          (SEQ ID NO 22)
MKIEEGKLVI WINGDKGYNG LAEVGKKFEK DTGIKVTVEH

PDKLEEKFPQ VAATGDGPDI IFWAHDRFGG YAQSGLLAEI

TPDKAFQDKL YPFTWDAVRY NGKLIAYPIA VEALSLIYNK

DLLPNPPKTW EEIPALDKEL KAKGKSALMF NLQEPYFTWP

LIAADGGYAF KYENGKYDIK DVGVDNAGAK AGLTFLVDLI

KNKHMNADTD YSIAEAAFNK GETAMTINGP WAWSNIDTSK
```

-continued

```
VNYGVTVLPT FKGQPSKPFV GVLSAGINAA SPNKELAKEF

LENYLLTDEG LEAVNKDKPL GAVALKSYEE ELAKDPRIAA

TMENAQKGEI MPNIPQMSAF WYAVRTAVIN AASGRQTVDE

ALKDAQTNSS SNNNNNNNNN NLGIEGRISE FGS QNVLSGR

RQHGAQGLSG YSGDNDWGYY GEAGAPGSDY SGSSGQWAPL

DFDYNSLPGL SGYNHEQQDY EEDSYRHVRS AGPITLQLDD

DDDDDSGIPI FEMDDEDEDS NDNQKFPLSF ERFPENEKNQ

VGHHHHHH.

MBPTB8N5 Protein length = 528 MW = 58232.8.
                                   (SEQ ID NO 23)
MKIEEGKLVI WINGDKGYNG LAEVGKKFEK DTGIKVTVEH

PDKLEEKFPQ VAATGDGPDI IFWAHDRFGG YAQSGLLAEI

TPDKAFQDKL YPFTWDAVRY NGKLIAYPIA VEALSLIYNK

DLLPNPPKTW EEIPALDKEL KAKGKSALMF NLQEPYFTWP

LIAADGGYAF KYENGKYDIK DVGVDNAGAK AGLTFLVDLI

KNKHMNADTD YSIAEAAFNK GETAMTINGP WAWSNIDTSK

VNYGVTVLPT FKGQPSKPFV GVLSAGINAA SPNKELAKEF

LENYLLTDEG LEAVNKDKPL GAVALKSYEE ELAKDPRIAA

TMENAQKGEI MPNIPQMSAF WYAVRTAVIN AASGRQTVDE

ALKDAQTNSS SNNNNNNNNN NLGIEGRISE FGS QNLVSGR

RQHGAQGLSG YSGDNDWGYY GEAGAPGSDY SGSSGQWAPL

DFDYNSLPGL SGYNHEQQDY EEDSYRHVRS AGPITLQLDD

DDDDDSGIPI FEMDDEDVDS NDNQKFPLSF ERFPENEKNQ

VGHHHHHH.
```

MPBTS8N5 has the same composition than MBPTS9N5, the difference between TS9 and TS8 is removed with the deletion.

Figure 1:
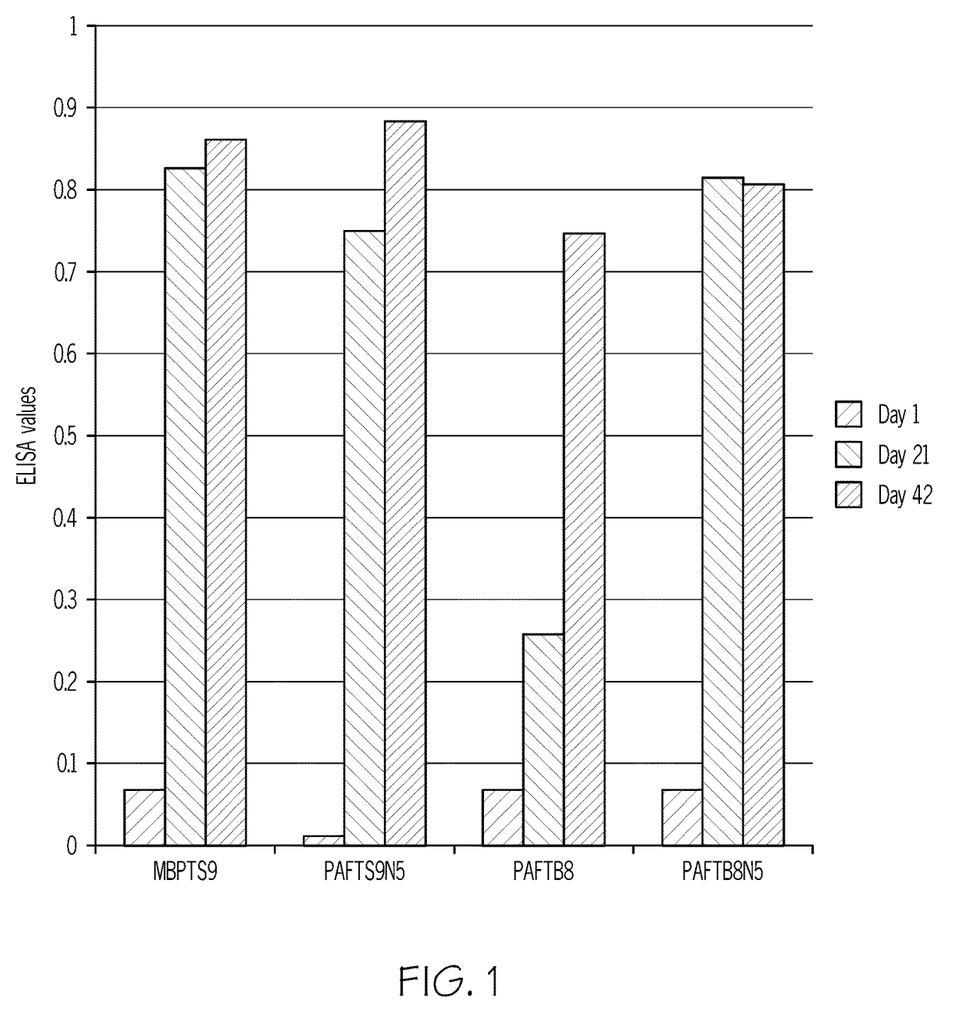
FIG. 1 depicts antibody titers following injection of MBPTS9, PAFTS9NS, PAFTB8 and PAFTB8N5.

MBPTS9, PAFTS9N5, PAFTB8 and PAFTB8N5 were mixed with a commercial adjuvant ENABL (Vaxliant Laboratories) and injected into 12 rabbits twice on Day 1 and 21. Blood samples were collected on Day 1, 21 and 42, the sera separated and the antibody titers determined by ELISA. The results are shown in FIG. 1. Other adjuvants known in the art may be used, including, for example, Al hydroxide and freund's adjuvant. In FIG. 1, the first bar indicates day 1, the second bar indicates day 21, the third bar indicates day 42. All antigens tested were very immunogenic, generating antibodies to Thrombostasin after only one injection. Surprisingly, the gene deletion did not affect the antibody production.

Figure 2:
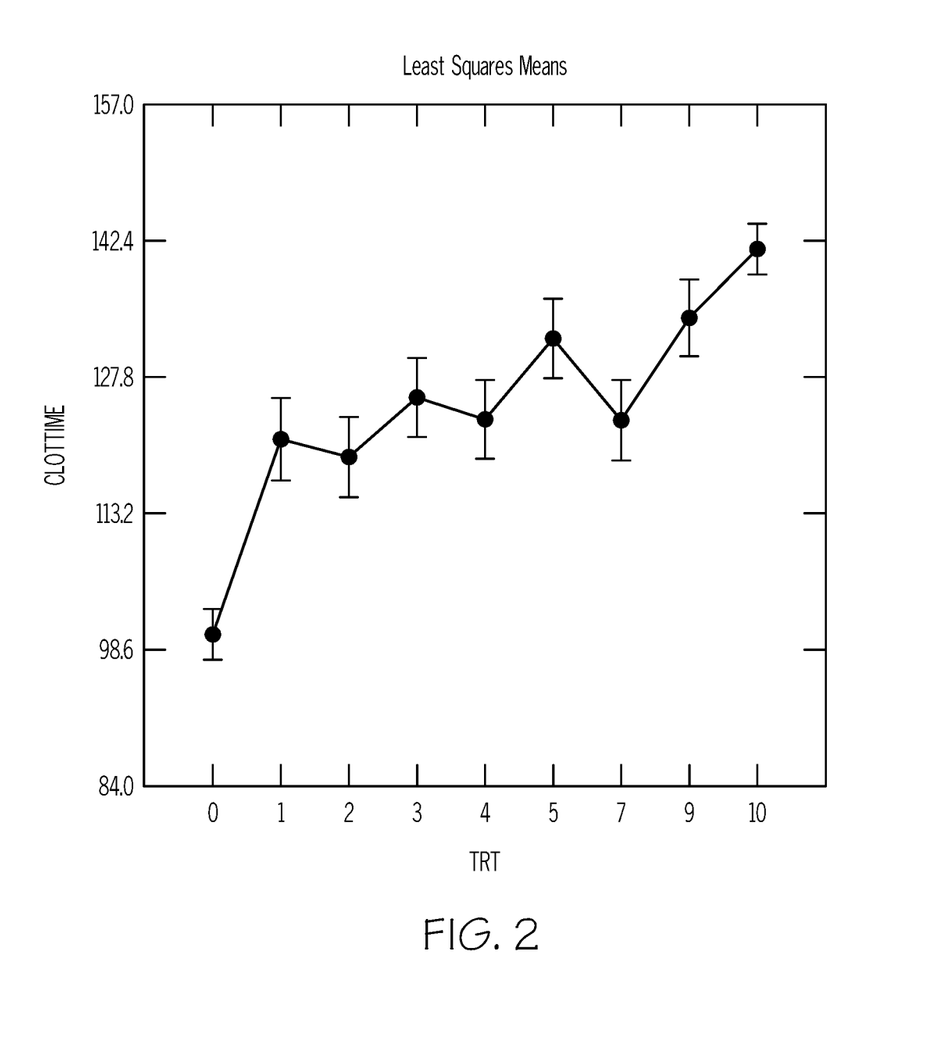
FIG. 2 depicts the ability of antibodies to inhibit the anticoagulant activity of Thrombostasin contained in the salivary glands of horn fly.

Finally, the antibodies were tested for the ability to inhibit the anticoagulant activity of Thrombostasin contained in the salivary glands of horn flies using the delay in recalcification time induced by horn fly saliva test (RCT). Briefly sample or control buffer, diluted in 50 mM Tris, pH 7.4 at 37° C., 0.15 M NaCl, 0.1% bovine serum albumin (BSA) and 0.1% polyethylene glycol) 8000 (PEG 8000) (TSBP buffer) were added to reference normal plasma (Accuclot, Sigma Chemical Company, St. Louis, MO); the mixture was incubated at 37° C. for 3 min before adding $CaCl_2$ solution (10 mM final concentration). The time between the addition of $CaCl_2$ and the first sign of the mass formation (clot) was recorded as clotting time. The results are summarized in FIG. 2, wherein Treatment 0: negative control, normal coagulation; Treatment 1: vaccinated with MBPTS9+saliva; Treatment 2: vaccinated with PAFTS9N5+saliva; Treatment 5: vaccinated with PAF TB8+saliva; Treatment 9: unvaccinated+saliva; Treatment 10: positive control saliva only. All vaccines inhibited the action of horn fly saliva. Treatment 2 (the truncated TS9N5 antigen) had the greatest effect. The unvaccinated group was not different from the positive control. Gene deletion of Thrombostasin at the C terminal end of the genes overcame the cell toxicity and increased the production of the proteins to commercially acceptable levels without changing the immunogenicity or the antigens or the biological activity of the antibodies generated by those antigens.

Example 2

PURPOSE—The purpose of this experiment is to evaluate the ability of an experimental vaccine using truncated thrombostasin antigens to generate antibody in cattle in cattle. The vaccine, composed 3 recombinant truncated TS antigens with adjuvant, will be injected intramuscularly into test animals. The antibody produce will be evaluated for their ability to neutralize the anti-coagulant activity of the saliva of horn flies.

VACCINE—The saliva of the horn fly, *Haematobia irritans irritans* contains thrombostasin proteins that prevent clotting of the blood of the bitten host, allowing the fly to continue to draw blood. The vaccine described in this example contains 3 recombinant proteins identified as MBPpTS9N5 (SEQ ID NO: 21), MBPpTS10N5 (SEQ ID NO:22) and MBPpTB8 N5 (SEQ ID NO: 23). MBP is a fusion protein used to enhance the immunogenicity of the vaccine, and TS9, TS10 and TB8 are isotypes of the thrombostasin proteins commonly found the saliva of horn flies in the USA. The vaccine stimulates the immune system to produce antibodies that mitigate the anti-clotting effects of the saliva of the horn fly.

Vaccine Administration
Route of exposure—Intramuscular injection of recombinant proteins suspended in a saline buffer with an added licensed adjuvant ENABL from VaxLiant.
Dose levels—100 μg of each of the above-mentioned protein mixed in an adjuvant.
Dose schedule—3 groups: group A vaccinated on day 0, group B vaccinated on day 0 and day 21, group C acting as control.
Calves
Species & breed—Bos torus and probably Angus or Angus crossbreeds
Sex—castrated males or intact females
Source—Local calf ranch
Age/weight—4-6 months old, 300-500 lbs
Number—11
Husbandry and Animal Care
Acclimation period—3-4 weeks
Housing—Corral
Environment—Opened and closed
Diet & water—Routine by New Mexico State University
Veterinary care—As provided by New Mexico State University EXPERIMENTAL DESIGN—11 calves are used in this experiment and randomized into two groups of four and one control group of three. An experimental vaccine consisting of 3 recombinant truncated thrombostasins with adjuvant is administered by intramuscular injection in the following treatments:
1. Single dose of the vaccine, day 0
2. Priming dose of vaccine, day 0 and booster on day 21
3. Control; 1 ml sterile saline, days 0 and 21

Blood is drawn on days 0, 21 and 35. Serum is be separated into 5 volumes of ½ cc and frozen. Antibody titers to the vaccine antigens is determined on sera collected on each day the blood is drawn. Serum titers of antibodies to the vaccine antigens is determined by an ELISA test.

VACCINE DESCRIPTION AND PREPARATION—Purified recombinant antigen(s) and adjuvants are suspended in an appropriate saline suspending agent.

Post Vaccination Animal Care

General health—Calves will be observed daily for adverse events related to vaccination and overall health.

Blood collection—Blood is collected from the jugular vein using a vacutainer tube and a 16-gauge needle while the animal is constrained in a squeeze chute. Serum is separated and processed for further use in antibody testing.

Analysis of Blood

Blood profile—Blood is drawn into red stoppered vacutainer tubes which allow for separation of cellular and fluid components of the blood.

Serum preservation—The separated serum is divided into small volumes (½ cc) in separate containers and frozen at −75 degrees F.

Antibody titer determination—Antibodies against the antigens in the vaccine are titered using an ELISA test. The antigens used in the test are the three truncated antigens and four full length thrombostasin protein TSS, TSB, TS9 and TS10.

Delay in recalcification time induced by horn fly saliva test (RCT): Briefly, sample or control buffer, diluted in 50 mM Tris, pH 7.4 at 37° C., 0.1 NaCl, 0.1% bovine serum albumin (BSA) and 0.1% polyethylene glycol 8000 (PEG 8000) (TSBP buffer) are added to reference normal plasma (Acculot Sigma Chemical Company, St Louis MO). The mixture is incubated at 37° C. for 3 minutes before adding $CaCl_2$ solution (10 mM final concentration. The time between the addition of $CaCl_2$ and the first sign of the mass formation (clot) was recorded as dotting time).

The results are shown in FIG. 3 and the Table below. The data show a number of positive effects: 1. The truncated proteins are antigenic, successfully producing antibodies in cattle despite the modifications. 2. A booster effect is observed after a primary and then a booster vaccination. 3. The truncated antigens appear to produce antibodies that react with the full-length antigens, indicating that antibodies to the full length or the truncated antigens will react with the particular isotype of thrombostasin in the saliva; the antibodies inhibit the biological effect of the thrombostasin and different antigens can be used in combination without interfering with antibody production. Applicant further found that the ELISA antibody titers are such that commercialization of the vaccine is possible. In one aspect, two vaccinations may be used—a primary and a booster vaccination.

Inhibition of the Anticoagulant Effect

| Calf # | Trt. | Clot Time | Saliva | Inh. Saliva |
| --- | --- | --- | --- | --- |
| 758 | A | 109.2 | 142.6 | −33.4 |
| 763 | A | 105.7 | 135.3 | −29.6 |
| 768 | A | 113.5 | 135.3 | −21.8 |
| 767 | A | 127 | 142.6 | −15.6 |
| Mean = | | 113.85 | 138.95 | −25.1 |
| 765 | B | 100.5 | 135.3 | −34.8 |
| 760 | B | 130.9 | 142.6 | −11.7 |
| 762 | B | 121.3 | 135.3 | −14 |
| 766 | B | 125.6 | 142.6 | −17 |
| Mean = | | 119.575 | 138.95 | −19.375 |
| 759 | C | 123.5 | 142.6 | −19.1 |
| 761 | C | 122.41 | 135.3 | −12.89 |
| 764 | C | 138 | 135.3 | 2.7 |
| Mean = | | 127.97 | 137.7333 | 9.76333333 |

Examining the data, it is clear that serum samples from vaccinated cattle were more effective in disrupting TS in horn fly saliva than were serum samples from the controls. Surprisingly, the serum from cattle vaccinated only once seem to be more effective the those from cattle vaccinated twice but the difference was not statistically significant (analysis of variance analysis p=0.186).

REFERENCES

M S Cupp et al. Evaluation of a recombinant salivary gland protein (thrombostasin) as a vaccine candidate to disrupt blood-feeding by horn flies. Vaccine 22: 2285-2297 (2004).

M S Cupp et al. Vaccination of cattle with recombinant salivary proteins of horn flies (Haematobiairritansirritans). Proc of World Assoc for Adv of Vet Parasit (WAAVP) Abstract 94 (2005).

M S Cupp et al Salivary gland thrombostasin isoforms differentially regulate blood uptake of horn flies on control and thrombostasin-vaccinated cattle. J. Med. Entomol. 47: 610-617 (2010).

All percentages and ratios are calculated by weight unless otherwise indicated.

All percentages and ratios are calculated based on the total composition unless otherwise indicated.

It should be understood that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "20 mm" is intended to mean "about 20 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications may be made without departing from the spirit and scope of the invention. It is therefore intended to cover in the appended claims all such changes and modifications that are within the scope of this invention.

What is claimed is:

1. A fusion protein comprising a. a truncated thrombostasin protein comprising a carboxy terminal deletion, wherein said truncated thrombostasin protein is selected from: SEQ ID NO: 13, SEQ ID NO: 14, and SEQ ID NO: 15, and combinations thereof; and
   b. a fusion partner protein comprising a non-thrombostasin protein component.

2. The truncated thrombostasin protein of claim 1, wherein said truncated thrombostasin protein is as immunogenic in mammals as a native, non-truncated thrombostasin protein.

3. The truncated thrombostasin protein of claim 1, wherein said truncated thrombostasin protein produce biologically active antibodies which interfere with an anti-clotting activity of natural thrombostasin from horn fly.

4. The fusion protein of claim 1, wherein said truncated thrombostasin protein composition additionally comprises an additional thrombostasin protein.

5. The fusion protein of claim 1, wherein said carboxy terminal deletion is a deletion of at least 5 amino acids, or at least 6 amino acids, or at least 7 amino acids, or at least 8 amino acids, or at least 9 amino acids, or at least 10 amino acids, or at least 11 amino acids, or at least 12 amino acids, or at least 13 amino acids, or at least 14 amino acids, or at least 15 amino acids, or from about 10 to 35 amino acids, or from about 15 to 30 amino acids, or about 20 to about 25 amino acids, or about 30 amino acids.

6. The fusion protein of claim 1, wherein said fusion partner protein is selected from maltose binding protein (MBP), protein for antigen fusion (PAF), C reactive protein (CRP) or a fragment thereof, β-galactosidase, glutathione-S-transferase, poly-histidine, myelin basic protein (MBP1-9) or a fragment thereof, chicken egg white ovalbumin (OVA) and combinations thereof.

7. The fusion protein of claim 1, wherein the truncated thrombostasin protein is SEQ ID NO: 13.

8. The fusion protein of claim 1, wherein the truncated thrombostasin protein is SEQ ID NO: 14.

9. The fusion protein of claim 1, wherein the truncated thrombostasin protein is SEQ ID NO: 15.

* * * * *

```
                             SEQUENCE LISTING

Sequence total quantity: 24
SEQ ID NO: 1            moltype = AA  length = 157
FEATURE                 Location/Qualifiers
source                  1..157
                        mol_type = protein
                        organism = Haematobia irritans
SEQUENCE: 1
QNVLSGRRQH GAQGLSGYSG DNDWGYYGEA GAPGSDYSGS SGQWAPLDFD YNSLPGLSGY   60
NHEQQDYEED SYRHVRSAGP ITLQLDDDDD DDSGIPIFEM DDEDEDSNDN QKFPLSFERF  120
PENEKNQEGL RARFNKFMAK FTSLFGRRRG VDVPNAA                           157

SEQ ID NO: 2            moltype = AA  length = 157
FEATURE                 Location/Qualifiers
source                  1..157
                        mol_type = protein
                        organism = Haematobia irritans
SEQUENCE: 2
QNVLSGRRQH GAQGLSGYSG DNDWGYYGEA GAPGSDYSGS SGQWAPLDFD YNSLPGLSGY   60
NHEQQDYEED SYRHVRSAGP ITLQLDDDDD DDSGIPIFEM DDEDEDSNDN QKFPLSFERF  120
PENEKNQVGL RARFNKFMAK FTSLFGRRRG VNVPNAA                           157

SEQ ID NO: 3            moltype = AA  length = 157
FEATURE                 Location/Qualifiers
source                  1..157
                        mol_type = protein
                        organism = Haematobia irritans
SEQUENCE: 3
QNLVSGRRQH GAQGLSGYSG DNDWGYYGEA GAPGSDYSGS SGQWAPLDFD YNSLPGLSGY   60
NHEQQDYEED SYRHVRSAGP ITLQLDDDDD DDSGIPIFEM DDEDVDSNDN QKFPLSFERF  120
PENEKNQVGL RARFNKFMAK FTSLFGRRRG VNVPNAA                           157

SEQ ID NO: 4            moltype = AA  length = 157
FEATURE                 Location/Qualifiers
source                  1..157
                        mol_type = protein
                        organism = Haematobia irritans
SEQUENCE: 4
QNVLSGRRQH GAQGLSGYSG DNDWGYYGEA GAPGSDYSGS SGQWAPLDFD YNSLPGLSGY   60
NHEQQDYEED SYRHVRSAGP ITLQLDDDDD DDSGIPIFEM DDEDEDSNDN QKFPLSFERF  120
PENEKNQEGL RARFNKFMAK FTSLFGRRRS VDVPNAA                           157

SEQ ID NO: 5            moltype = AA  length = 157
FEATURE                 Location/Qualifiers
source                  1..157
                        mol_type = protein
                        organism = Haematobia irritans
SEQUENCE: 5
QNVLSGRRQH GAQGLSGYSG DNDWGYYGEA GAPGSDYSGS SGQWAPLDFD YNSLPGLSGY   60
NHEQQDYEED SYRHVRSAGP ITLQLNDDDD DDSGIPIFEM DDEDEDSNDN QKFPLSFERF  120
PENEKNQEGL RARFNKFMAK FTSLFGRRRG VDVPNAA                           157

SEQ ID NO: 6            moltype = AA  length = 157
FEATURE                 Location/Qualifiers
source                  1..157
                        mol_type = protein
                        organism = Haematobia irritans
SEQUENCE: 6
QNVLSGRRQH GAQGLSGYSG DNDWGYYGEA GAPGSDYSGS SGQWAPLDFD YNSLPGLSGY   60
NHEQQDYEED SYRHVRSAGP ITLQLDDDDD DDSGIPIFEM DDEDEDSNDN QKFPLSFERF  120
PENEKNQVGL RARFNKFMAK FTSLFGRRRG VDVPNAA                           157

SEQ ID NO: 7            moltype = AA  length = 157
FEATURE                 Location/Qualifiers
source                  1..157
                        mol_type = protein
                        organism = Haematobia irritans
SEQUENCE: 7
QNVLSGRRQH GAQGLSGYSG DNDWGYYGEA GAPGSDYSGS SGQWAPLDFD YNSLPGLSGY   60
NHEQQDYEED SYRHVRSAGP ITLQLDDDDD DDSGIPIFEM DDEDEDSNDN QKFPLSFERF  120
PENEKNQEGL RARFNKFMAK FTSLFGRRRG VNVPNAA                           157
```

```
SEQ ID NO: 8              moltype = AA  length = 157
FEATURE                   Location/Qualifiers
source                    1..157
                          mol_type = protein
                          organism = Haematobia irritans
SEQUENCE: 8
QNVLSGRRQH GAQGLSGYSG DNDWGYYGEA GAPGSDYSGS SGQWAPLDFD YNSLPGLSGY    60
NHEQQDYEED SYRHVRSAGP ITLQLDDDDD DDSGIPIFEM DDEDEDSNDN QKFPLSFERF   120
PENEKNQEGL RARFNKFMAK FTSLFGRRRS VNVPNAA                            157

SEQ ID NO: 9              moltype = AA  length = 157
FEATURE                   Location/Qualifiers
source                    1..157
                          mol_type = protein
                          organism = Haematobia irritans
SEQUENCE: 9
QNVLSGRRQH GAQGLSGYSG DNDWGYYGEA GAPGSDYSGS SGQWAPLDFD YNSLPGLSGY    60
NHEQQDYEED SYRHVRSAGP ITLQLDDDDD DDSGIPIFEM DDEDEDSNDN QKFPLSFERF   120
PENEKNQVGL RARFNKFMAK FTSLFGRRRG VDVPNAA                            157

SEQ ID NO: 10             moltype = AA  length = 157
FEATURE                   Location/Qualifiers
source                    1..157
                          mol_type = protein
                          organism = Haematobia irritans
SEQUENCE: 10
QNVLSGRRQH GAQGLSGYSG DNDWGYYGEA GAPGSDYSGS SGQWAPLDFD YNSLPGLSGY    60
NHEQQDYEED SYRHVRSAGP ITLQLDDDDD DDSGIPIFEM DDEDEDSNDN QKFPLSFERF   120
PENEKNQQGL RARFNKFMAK FTSLFGRRRG VDVPNAA                            157

SEQ ID NO: 11             moltype = AA  length = 157
FEATURE                   Location/Qualifiers
source                    1..157
                          mol_type = protein
                          organism = Haematobia irritans
SEQUENCE: 11
QNVLSGRRQH GAQGLSGYSG DNDWGYYGEA GAPGSDYSGS SGQWAPLDFD YNSLPGLSGY    60
NHEQQDYEED SYRHVRSAGP ITLQLDDDDD DDSGIPIFEM DDEDEDSNDN QKFPLSFERF   120
PENEKNQLGL RARFNKFMAK FTSLFGRRRG VDVPNAA                            157

SEQ ID NO: 12             moltype = AA  length = 157
FEATURE                   Location/Qualifiers
source                    1..157
                          mol_type = protein
                          organism = Haematobia irritans
SEQUENCE: 12
QNVLSGRRQH GAQGLSGYSG DNDWGYYGEA GAPGSDYSGS SGQWAPLDFD YNSLPGLSGY    60
NHEQQDYEED SYRHVRSAGP ITLQLDDDDD DDSGIPIFEM DDEDEDSNDN QKFPLSFERF   120
PENEKNQVGL RARFNKFMAK FTSLFGRRRS VNVPNAA                            157

SEQ ID NO: 13             moltype = AA  length = 135
FEATURE                   Location/Qualifiers
source                    1..135
                          mol_type = protein
                          organism = Haematobia irritans
SEQUENCE: 13
QNLVSGRRQH GAQGLSGYSG DNDWGYYGEA GAPGSDYSGS SGQWAPLDFD YNSLPGLSGY    60
NHEQQDYEED SYRHVRSAGP ITLQLDDDDD DDSGIPIFEM DDEDVDSNDN QKFPLSFERF   120
PENEKNQVGH HHHHH                                                    135

SEQ ID NO: 14             moltype = AA  length = 135
FEATURE                   Location/Qualifiers
source                    1..135
                          mol_type = protein
                          organism = Haematobia irritans
SEQUENCE: 14
QNVLSGRRQH GAQGLSGYSG DNDWGYYGEA GAPGSDYSGS SGQWAPLDFD YNSLPGLSGY    60
NHEQQDYEED SYRHVRSAGP ITLQLDDDDD DDSGIPIFEM DDEDEDSNDN QKFPLSFERF   120
PENEKNQEGH HHHHH                                                    135

SEQ ID NO: 15             moltype = AA  length = 135
FEATURE                   Location/Qualifiers
source                    1..135
                          mol_type = protein
                          organism = Haematobia irritans
SEQUENCE: 15
QNVLSGRRQH GAQGLSGYSG DNDWGYYGEA GAPGSDYSGS SGQWAPLDFD YNSLPGLSGY    60
NHEQQDYEED SYRHVRSAGP ITLQLDDDDD DDSGIPIFEM DDEDEDSNDN QKFPLSFERF   120
PENEKNQVGH HHHHH                                                    135
```

```
SEQ ID NO: 16              moltype = AA   length = 556
FEATURE                    Location/Qualifiers
REGION                     1..556
                           note = MBP-TS9 (Fusion Protein - MBP + TS9)
source                     1..556
                           mol_type = protein
                           organism = synthetic construct
SEQUENCE: 16
MKIEEGKLVI WINGDKGYNG LAEVGKKFEK DTGIKVTVEH PDKLEEKFPQ VAATGDGPDI    60
IFWAHDRFGG YAQSGLLAEI TPDKAFQDKL YPFTWDAVRY NGKLIAYPIA VEALSLIYNK   120
DLLPNPPKTW EEIPALDKEL KAKGKSALMF NLQEPYFTWP LIAADGGYAF KYENGKYDIK   180
DVGVDNAGAK AGLTFLVDLI KNKHMNADTD YSIAEAAFNK GETAMTINGP WAWSNIDTSK   240
VNYGVTVLPT FKGQPSKPFV GVLSAGINAA SPNKELAKEF LENYLLTDEG LEAVNKDKPL   300
GAVALKSYEE ELAKDPRIAA TMENAQKGEI MPNIPQMSAF WYAVRTAVIN AASGRQTVDE   360
ALKDAQTNSS SNNNNNNNNN NLGIEGRISE FGSQNVLSGR RQHGAQGLSG YSGDNDWGYY   420
GEAGAPGSDY SGSSSGQWAPL DFDYNSLPGL SGYNHEQQDY EEDSYRHVRS AGPITLQLDD   480
DDDDDSGIPI FEMDDEDEDS NDNQKFPLSF ERFPENEKNQ EGLRARFNKF MAKFTSLFGR   540
RRGVDVPNAA HHHHHH                                                 556

SEQ ID NO: 17              moltype = AA   length = 304
FEATURE                    Location/Qualifiers
REGION                     1..304
                           note = PAF-TS9 (Fusion Protein - PAF + TS9) Protein
source                     1..304
                           mol_type = protein
                           organism = synthetic construct
SEQUENCE: 17
MKLTIESTPF NVAEGKEVLL LVHNLPQHLF GYSWYKGERV DGNRQIIGYV IGTQQATPGP    60
AYSGREIIYP NASLLIQNII QNDTGFYTLH VIKSDLVNEE ATGQFRVYPE LPKPSISSNN   120
SKPVEDKDAV AFTCEPETQD AQNVLSGRRQ HGAQGLSGYS GDNDWGYYGE AGAPGSDYSG   180
SSGQWAPLDF DYNSLPGLSG YNHEQQDYEE DSYRHVRSAG PITLQLDDDD DDDSGIPIFE   240
MDDEDEDSND NQKFPLSFER FPENEKNQEG LRARFNKFMA KFTSLFGRRR GVDVPNAAHH   300
HHHH                                                              304

SEQ ID NO: 18              moltype = AA   length = 276
FEATURE                    Location/Qualifiers
REGION                     1..276
                           note = PAF-TS9N5 (Fusion Protein - PAF + Truncated TS9)
                            Protein
source                     1..276
                           mol_type = protein
                           organism = synthetic construct
SEQUENCE: 18
MKLTIESTPF NVAEGKEVLL LVHNLPQHLF GYSWYKGERV DGNRQIIGYV IGTQQATPGP    60
AYSGREIIYP NASLLIQNII QNDTGFYTLH VIKSDLVNEE ATGQFRVYPE LPKPSISSNN   120
SKPVEDKDAV AFTCEPETQD AQNVLSGRRQ HGAQGLSGYS GDNDWGYYGE AGAPGSDYSG   180
SSGQWAPLDF DYNSLPGLSG YNHEQQDYEE DSYRHVRSAG PITLQLDDDD DDDSGIPIFE   240
MDDEDEDSND NQKFPLSFER FPENEKNQEG HHHHHH                            276

SEQ ID NO: 19              moltype = AA   length = 304
FEATURE                    Location/Qualifiers
REGION                     1..304
                           note = PAF-TB8 (Fusion Protein - PAF + TB8) Protein
source                     1..304
                           mol_type = protein
                           organism = synthetic construct
SEQUENCE: 19
MKLTIESTPF NVAEGKEVLL LVHNLPQHLF GYSWYKGERV DGNRQIIGYV IGTQQATPGP    60
AYSGREIIYP NASLLIQNII QNDTGFYTLH VIKSDLVNEE ATGQFRVYPE LPKPSISSNN   120
SKPVEDKDAV AFTCEPETQD AQNVLSGRRQ HGAQGLSGYS GDNDWGYYGE AGAPGSDYSG   180
SSGQWAPLDF DYNSLPGLSG YNHEQQDYEE DSYRHVRSAG PITLQLDDDD DDDSGIPIFE   240
MDDEDVDSND NQKFPLSFER FPENEKNQVG LRARFNKFMA KFTSLFGRRR GVNVPNAAHH   300
HHHH                                                              304

SEQ ID NO: 20              moltype = AA   length = 276
FEATURE                    Location/Qualifiers
REGION                     1..276
                           note = PAF-TB8N5 (Fusion Protein - PAF + Truncated TB8)
                            Protein
source                     1..276
                           mol_type = protein
                           organism = synthetic construct
SEQUENCE: 20
MKLTIESTPF NVAEGKEVLL LVHNLPQHLF GYSWYKGERV DGNRQIIGYV IGTQQATPGP    60
AYSGREIIYP NASLLIQNII QNDTGFYTLH VIKSDLVNEE ATGQFRVYPE LPKPSISSNN   120
SKPVEDKDAV AFTCEPETQD AQNVLSGRRQ HGAQGLSGYS GDNDWGYYGE AGAPGSDYSG   180
SSGQWAPLDF DYNSLPGLSG YNHEQQDYEE DSYRHVRSAG PITLQLDDDD DDDSGIPIFE   240
MDDEDVDSND NQKFPLSFER FPENEKNQVG HHHHHH                            276
```

```
SEQ ID NO: 21           moltype = AA  length = 528
FEATURE                 Location/Qualifiers
REGION                  1..528
                        note = MBP-TS9N5 Protein
source                  1..528
                        mol_type = protein
                        organism = synthetic construct
SEQUENCE: 21
MKIEEGKLVI WINGDKGYNG LAEVGKKFEK DTGIKVTVEH PDKLEEKFPQ VAATGDGPDI    60
IFWAHDRFGG YAQSGLLAEI TPDKAFQDKL YPFTWDAVRY NGKLIAYPIA VEALSLIYNK   120
DLLPNPPKTW EEIPALDKEL KAKGKSALMF NLQEPYFTWP LIAADGGYAF KYENGKYDIK   180
DVGVDNAGAK AGLTFLVDLI KNKHMNADTD YSIAEAAFNK GETAMTINGP WAWSNIDTSK   240
VNYGVTVLPT FKGQPSKPFV GVLSAGINAA SPNKELAKEF LENYLLTDEG LEAVNKDKPL   300
GAVALKSYEE ELAKDPRIAA TMENAQKGEI MPNIPQMSAF WYAVRTAVIN AASGRQTVDE   360
ALKDAQTNSS SNNNNNNNNN NLGIEGRISE FGSQNVLSGR RQHGAQGLSG YSGDNDWGYY   420
GEAGAPGSDY SGSSGQWAPL DFDYNSLPGL SGYNHEQQDY EEDSYRHVRS AGPITLQLDD   480
DDDDDSGIPI FEMDDEDEDS NDNQKFPLSF ERFPENEKNQ EGHHHHHH              528

SEQ ID NO: 22           moltype = AA  length = 528
FEATURE                 Location/Qualifiers
REGION                  1..528
                        note = MBP-TS10N5 Protein
source                  1..528
                        mol_type = protein
                        organism = synthetic construct
SEQUENCE: 22
MKIEEGKLVI WINGDKGYNG LAEVGKKFEK DTGIKVTVEH PDKLEEKFPQ VAATGDGPDI    60
IFWAHDRFGG YAQSGLLAEI TPDKAFQDKL YPFTWDAVRY NGKLIAYPIA VEALSLIYNK   120
DLLPNPPKTW EEIPALDKEL KAKGKSALMF NLQEPYFTWP LIAADGGYAF KYENGKYDIK   180
DVGVDNAGAK AGLTFLVDLI KNKHMNADTD YSIAEAAFNK GETAMTINGP WAWSNIDTSK   240
VNYGVTVLPT FKGQPSKPFV GVLSAGINAA SPNKELAKEF LENYLLTDEG LEAVNKDKPL   300
GAVALKSYEE ELAKDPRIAA TMENAQKGEI MPNIPQMSAF WYAVRTAVIN AASGRQTVDE   360
ALKDAQTNSS SNNNNNNNNN NLGIEGRISE FGSQNVLSGR RQHGAQGLSG YSGDNDWGYY   420
GEAGAPGSDY SGSSGQWAPL DFDYNSLPGL SGYNHEQQDY EEDSYRHVRS AGPITLQLDD   480
DDDDDSGIPI FEMDDEDEDS NDNQKFPLSF ERFPENEKNQ VGHHHHHH              528

SEQ ID NO: 23           moltype = AA  length = 528
FEATURE                 Location/Qualifiers
REGION                  1..528
                        note = MBP-TB8N5 Protein
source                  1..528
                        mol_type = protein
                        organism = synthetic construct
SEQUENCE: 23
MKIEEGKLVI WINGDKGYNG LAEVGKKFEK DTGIKVTVEH PDKLEEKFPQ VAATGDGPDI    60
IFWAHDRFGG YAQSGLLAEI TPDKAFQDKL YPFTWDAVRY NGKLIAYPIA VEALSLIYNK   120
DLLPNPPKTW EEIPALDKEL KAKGKSALMF NLQEPYFTWP LIAADGGYAF KYENGKYDIK   180
DVGVDNAGAK AGLTFLVDLI KNKHMNADTD YSIAEAAFNK GETAMTINGP WAWSNIDTSK   240
VNYGVTVLPT FKGQPSKPFV GVLSAGINAA SPNKELAKEF LENYLLTDEG LEAVNKDKPL   300
GAVALKSYEE ELAKDPRIAA TMENAQKGEI MPNIPQMSAF WYAVRTAVIN AASGRQTVDE   360
ALKDAQTNSS SNNNNNNNNN NLGIEGRISE FGSQNVLSGR RQHGAQGLSG YSGDNDWGYY   420
GEAGAPGSDY SGSSGQWAPL DFDYNSLPGL SGYNHEQQDY EEDSYRHVRS AGPITLQLDD   480
DDDDDSGIPI FEMDDEDVDS NDNQKFPLSF ERFPENEKNQ VGHHHHHH              528

SEQ ID NO: 24           moltype = AA  length = 30
FEATURE                 Location/Qualifiers
REGION                  1..30
                        note = TS9 Deletion
source                  1..30
                        mol_type = protein
                        organism = synthetic construct
SEQUENCE: 24
LRARFNKFMA KFTSLFGRRR GVDVPNAAHH                                    30
```